US012036011B2

(12) United States Patent
Flower et al.

(10) Patent No.: US 12,036,011 B2
(45) Date of Patent: *Jul. 16, 2024

(54) QUANTIFICATION OF ABSOLUTE BLOOD FLOW IN TISSUE USING FLUORESCENCE-MEDIATED PHOTOPLETHYSMOGRAPHY

(71) Applicant: Stryker Corporation, Kalamazoo, MI (US)

(72) Inventors: Robert W. Flower, Hunt Valley, MD (US); Robert Anthony Stead, Vancouver (CA); Arthur E. Bailey, North Vancouver (CA)

(73) Assignee: Stryker Corporation, Kalamazoo, MI (US)

( * ) Notice: Subject to any disclaimer, the term of this patent is extended or adjusted under 35 U.S.C. 154(b) by 992 days.

This patent is subject to a terminal disclaimer.

(21) Appl. No.: 16/859,842

(22) Filed: Apr. 27, 2020

(65) Prior Publication Data

US 2020/0323439 A1    Oct. 15, 2020

Related U.S. Application Data

(63) Continuation of application No. 15/517,895, filed as application No. PCT/IB2014/065189 on Oct. 9, 2014, now Pat. No. 10,631,746.

(51) Int. Cl.
*A61B 5/026* (2006.01)
*A61B 5/00* (2006.01)
(Continued)

(52) U.S. Cl.
CPC .......... *A61B 5/0261* (2013.01); *A61B 5/0071* (2013.01); *A61B 5/0275* (2013.01);
(Continued)

(58) Field of Classification Search
CPC ... A61B 5/0261; A61B 5/0071; A61B 5/0275; A61B 5/0295; A61B 5/00; A61B 5/6826
See application file for complete search history.

(56) References Cited

U.S. PATENT DOCUMENTS

2008/0294096 A1\* 11/2008 Uber, III ............. A61M 31/005
604/66
2011/0060181 A1\* 3/2011 Altman ............... A61M 60/427
600/37

(Continued)

*Primary Examiner* — Sean P Dougherty
(74) *Attorney, Agent, or Firm* — Morrison & Foerster LLP (57) ABSTRACT

A method, an apparatus, and a kit including the apparatus and a fluorescence agent are provided for measuring a time-varying change in an amount of blood in a tissue volume, and include exciting a fluorescence agent in the blood, acquiring a time-varying light intensity signal during a pulsatile flow of the blood through the tissue volume, the pulsatile flow having a systolic and a diastolic phase resembling a conventional photoplethysmogram, and processing the acquired signal by applying a modified Beer-Lambert law to obtain a measurement of the time-varying change in the amount of blood in the tissue volume. The instantaneous molar concentration of the fluorescence agent is determined by utilizing a concentration-mediated change in a fluorescence emission spectrum of the fluorescence agent. There is further provided a fluorescence agent for use in the method.

21 Claims, 10 Drawing Sheets (51) Int. Cl.
*A61B 5/0275* (2006.01)
*A61B 5/0295* (2006.01)
(52) U.S. Cl.
CPC ............. *A61B 5/0295* (2013.01); *A61B 5/00* (2013.01); *A61B 5/6826* (2013.01)

(56) References Cited

U.S. PATENT DOCUMENTS

2015/0182137 A1\* 7/2015 Flower ................. A61B 5/0071
  600/431
2017/0245766 A1\* 8/2017 Flower ................. A61B 5/6826

\* cited by examiner

QUANTIFICATION OF ABSOLUTE BLOOD FLOW IN TISSUE USING FLUORESCENCE-MEDIATED PHOTOPLETHYSMOGRAPHY

CROSS-REFERENCE TO RELATED APPLICATIONS

This application is a continuation of U.S. patent application Ser. No. 15/517,895, filed Apr. 7, 2017, which is a national stage application under 35 USC 371 of International Application No. PCT/IB2014/065189, filed Oct. 9, 2014, the entire contents of each of which are incorporated herein by reference.

FIELD OF THE INVENTION

The present invention relates generally to the field of optical assessment of blood flow in tissue using photoplethysmography (PPG), and in particular to the quantitative assessment of blood flow in tissue, including microvascular blood flow in tissue.

BACKGROUND OF THE INVENTION

Perfusion refers to the flow of blood into and out of the tissue capillary bed. Quantification of tissue perfusion is of interest to clinicians across many surgical and non-surgical specialties. Although simple binary assessment (flow versus no-flow) may be adequate for some clinical applications, quantification of perfusion in standard measures is desirable in many other clinical applications. To date, quantitative assessment of tissue perfusion has remained elusive.

Photoplethysmography (PPG) is an optical technique that can be used to estimate changes in microvascular blood volume, and PPG-based technology has been deployed in commercially available medical devices for assessing pulse rate, oxygen saturation, blood pressure, and cardiac output. A typical output of such devices is the PPG waveform that corresponds to the heartbeat of the subject. Despite the relatively wide application of PPG technology to such medical devices, PPG has not been utilized to provide measurements in standardized units when assessing blood flow. A PPG technology with such capabilities would enable routine measurements of blood flow in tissue, including perfusion measurements, to be made in standardized units of volume/unit time/tissue area. This would be of significant value to clinicians, as such measurements would allow direct inter-site and inter-subject comparisons.

SUMMARY OF THE INVENTION

In accordance with a first aspect of the invention, there is provided a method for measuring a time-varying change in an amount of blood in a tissue volume. The method includes exciting a fluorescence agent in the blood, such as for example indocyanine green (ICG), acquiring a time-varying light intensity signal during a pulsatile flow of the blood through the tissue volume, wherein the pulsatile flow has a diastolic and a systolic phase resembling a conventional photoplethysmogram, and processing the acquired time-varying light intensity signal to obtain a measurement of the time-varying change in the amount of blood in the tissue volume.

In the first aspect, the method may exclude any step of administering the fluorescence agent to a subject.

Furthermore, in the first aspect, the method may exclude correlating the measurement of the time-varying change in the amount of blood in the tissue volume to a physiological parameter, a diagnostic parameter, or a pathological parameter.

In accordance with a second aspect, there is provided an apparatus for measuring a time-varying change in an amount of blood in a tissue volume. The apparatus includes means for exciting a fluorescence agent in the blood, such as for example ICG, means for acquiring a time-varying light intensity signal during a pulsatile flow of the blood through the tissue volume, wherein the pulsatile flow has a diastolic and a systolic phase resembling a conventional photoplethysmogram, and means for processing the acquired time-varying light intensity signal to obtain a measurement of the time-varying change in the amount of blood in the tissue volume.

In a third aspect, there is provided a kit for measuring a time-varying change in an amount of blood in a tissue volume, the kit including the apparatus of the second aspect and a fluorescence agent such as, for example, ICG.

In a fourth aspect, there is provided a fluorescence agent for use in a method for measuring a time-varying change in an amount of blood in a tissue volume of a subject, the method being according to the first aspect.

In the various aspects of the present invention, a modified Beer Lambert law is applied at the diastolic and systolic phases of the pulsatile flow of blood through tissue volume such that:

$$\Delta L = \ln[(I_e\Phi - I_m/I_e\Phi - I_p)](\varepsilon C)^{-1}$$

where $\Delta L$ is a change in aggregate blood layer thickness within a given tissue volume, $I_e$ is an intensity of an excitation light exciting the fluorescence agent in the blood, $\Phi$ is a quantum efficiency of the fluorescence agent, $I_m$ is an intensity of the time-varying light intensity signal during the diastolic phase minimum of the pulsatile flow of the blood through the tissue volume, $I_p$ is an intensity of the time-varying light intensity signal during the systolic phase maximum of the pulsatile flow of the blood through the tissue volume, $\varepsilon$ is a molar absorption coefficient for the fluorescence agent, and $C$ is an instantaneous molar concentration of the fluorescence agent in the blood.

In the various aspects of the present invention, the instantaneous molar concentration of the fluorescence agent in the blood is preferably determined by utilizing a concentration-mediated change in a fluorescence emission spectrum of the fluorescence agent. The concentration-mediated change in fluorescence emission spectrum of the fluorescence agent includes a monotonic spectral shift.

In various aspects of the present invention, utilizing the concentration-mediated change in fluorescence emission spectrum of the fluorescence agent preferably includes selecting first and second spectral bands of fluorescence emission spectrum of the fluorescence agent, acquiring first and second intensities of fluorescence emission integrated over wavelengths in the first and second spectral bands respectively, calculating a ratio of the first and second intensities, and deriving a value for C from the ratio. In various embodiments, the first spectral band includes wavelengths ranging from about 780 nm to about 835 nm, or a subset thereof, and the second spectral band includes wavelengths ranging from about 835 nm to about 1000 nm, or a subset thereof.

According to an embodiment, the first and second spectral bands are selected such that one of the first and second intensities varies monotonically with C, and one of the first and second intensities is unchanged with C. In another embodiment, the first and second spectral bands are selected such that the first and second intensities increase monotonically with C, but at different rates. In yet further embodiment, the first and second spectral bands are selected such that the first intensity increases monotonically with C, and the second intensity decreases monotonically with C. The instantaneous molar concentration of the fluorescence agent in blood ranges in various embodiments from about 2 μM to about 10 mM.

The optional features of the invention set out above may be applied, in any combination, with any aspect of the invention, unless the context demands otherwise.

Further optional features of the invention are set out below.

BRIEF DESCRIPTION OF THE DRAWINGS

In accompanying drawings which illustrate embodiments of the invention.

DETAILED DESCRIPTION OF THE INVENTION

Reference will now be made in detail to implementations and embodiments of various aspects and variations of the invention, examples of which are illustrated in the accompanying drawings.

Figure 1:
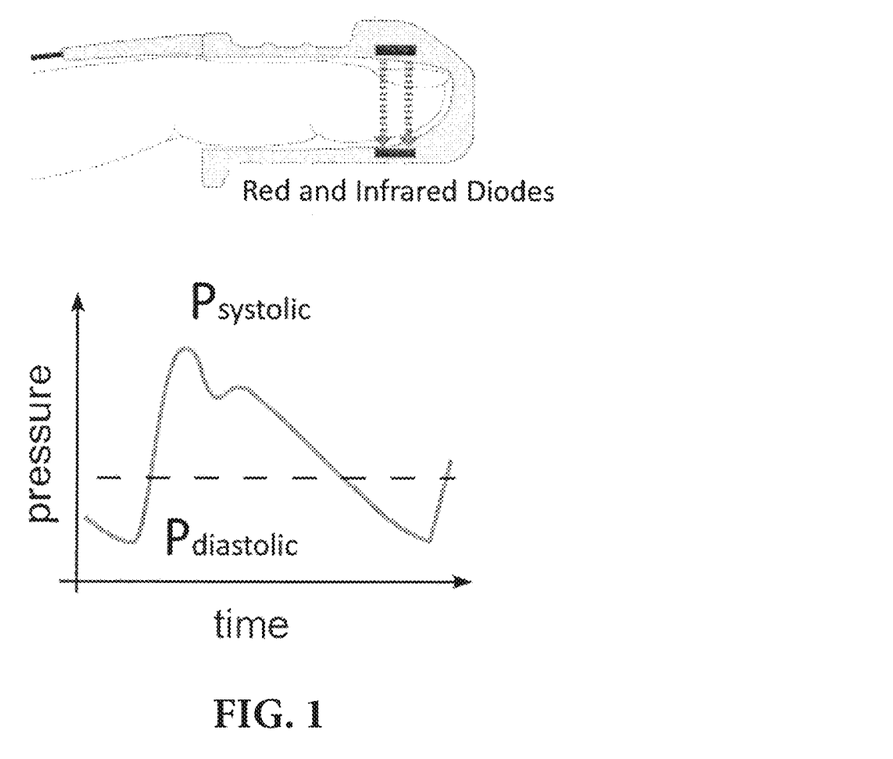
FIG. 1 schematically illustrates the use of conventional photoplethysmography (PPG) in which a fingertip sensor is used to measure pulse rate, blood oxygen saturation or both.

Conventional photoplethysmography (PPG) can estimate changes in tissue blood volume by detecting changes in the amount of red or near-infrared light transmitted through the tissue. As the blood volume within tissue expands and contracts during a cardiovascular pressure pulse corresponding to the heartbeat of the subject, the amount of light absorbed by the blood volume increases and decreases, respectively. As shown in FIG. 1, for example, the aggregate blood volume in the fingertip blood vessels is smallest during cardiovascular pressure pulse diastole and the volume is greatest during systole. Although it may be used for measuring pulse rate and blood oxygenation, this application of PPG technology is not configured to provide volumetric flow measurements in standardized units.

To be able to provide volumetric microvascular blood flow measurements in standardized units, the metrics of the PPG waveform must be related in a known and repeatable fashion to the blood volume changes in the tissue. It is possible to establish this type of deterministic relationship with the application of a modified Beer-Lambert law (also known as Beer's law, or the Beer-Lambert-Bouguer law). The Beer-Lambert law relates the attenuation of a light beam passing through a medium to the path length through the medium and its absorptivity and this relationship utilized in conventional PPG. Conventional PPG is performed by passing a beam of near-IR wavelengths of light through tissue (e.g., a fingertip), but the need for trans-illumination of tissue significantly limits application of this method to the more general case of volumetric blood flow measurements in tissue. According to an embodiment, the present invention utilizes a modified Beer-Lambert law to enable such blood flow measurements using fluorescent light wavelengths emitted by a fluorescence agent such as a fluorescence dye. Such a dye may, for example, be bound preferentially to blood plasma, thereby making it possible to position both the light beam source and fluorescent light detector on the surface of the tissue. The fluorescent light emitted from, for example, the dye-tagged plasma component of blood will conform to the modified Beer-Lambert law and, by solving the equation for the optical path length and quantifying the respective parameters, fluorescence-mediated PPG is capable of providing volumetric blood flow measurements, including microvascular blood flow measurements without trans-illumination.

Thus, in contrast to the conventional PPG technology, the present invention provides fluorescence-mediated photoplethysmography (FM-PPG) for measuring time-varying changes in the amount of blood in a tissue volume, and presenting these changes as a blood flow, including microvascular blood flow, in standardized units (e.g., volume/unit time). With FM-PPG, according to the various embodiments, the detected fluorescence intensity is proportional to the instantaneous concentration of a fluorescence agent in the blood (e.g., a fluorescence agent in the blood plasma), and can thus be utilized to determine blood flow in tissue, including microvascular blood flow or perfusion. Blood flow in tissue is generally understood as an increase in the total amount of blood flowing into an anatomic structure or region; blood flow encompasses tissue perfusion or microvascular blood flow, which is the amount of blood flowing through the capillaries of the vascular bed of the anatomic structure or region. In various embodiments, the method and apparatus of the present invention are used for measuring blood flow in tissue, and more particularly, for measuring perfusion or microvascular blood flow in tissue. In various embodiments, the use of the method and apparatus of the present invention includes the ability to discriminate between the blood flow and the microvascular blood flow.

In accordance with one aspect of the invention, there is provided a method for measuring a time-varying change in an amount of blood in a tissue volume. The method comprises exciting a fluorescence agent in the blood, acquiring a time-varying light intensity signal, which includes a time-varying fluorescence intensity signal, during a pulsatile flow of the blood through the tissue volume, the pulsatile flow having a diastolic phase and a systolic phase resembling a conventional photoplethysmogram. The method further comprises processing the acquired time-varying light intensity signal to obtain a measurement of the time-varying change in the amount of blood in the tissue volume by applying a modified Beer-Lambert law at the diastolic and systolic phases.

In various embodiments, a suitable fluorescence agent is an agent which can circulate with the blood (e.g., an agent which can circulate with, for example a component of the blood such as plasma in the blood) and which fluoresces when exposed to appropriate excitation light energy. Furthermore, the fluorescence agent exhibits a concentration-mediated change in its fluorescence emission spectrum. In various embodiments, the concentration-mediated change includes a monotonic spectral shift in the fluorescence emission spectrum of the fluorescence agent. An example of the fluorescence agent is a fluorescence dye, which includes any non-toxic fluorescence dye exhibiting a monotonic spectral shift with concentration. In certain embodiments, the fluorescence dye is a dye that emits light in the near-infrared spectrum. In certain embodiments, the fluorescence dye is a tricarbocyanine dye such as, for example, indocyanine green (ICG). In other embodiments the fluorescence dye may further be or comprise fluorescein isothiocyanate, rhodamine, phycoerythrin, phycocyanin, allophycocyanin, o-phthaldehyde, fluorescamine, rose Bengal, trypan blue, fluoro-gold, or a combination thereof, using excitation light wavelengths appropriate to each dye. In some embodiments, an analogue or a derivative of the fluorescence dye may be used. For example, a fluorescence dye analog or a derivative includes a fluorescence dye that has been chemically modified, but still retains its ability to fluoresce when exposed to light energy of an appropriate wavelength.

One aspect of the method of measuring the time-varying change in the amount of blood in the tissue volume of the subject comprises administering the fluorescence agent to the subject such that the fluorescence agent circulates with the blood in the tissue volume as the blood flows through the tissue volume. In various embodiments, the fluorescence agent may be administered to the subject intravenously, e.g., as a bolus injection, in a suitable concentration for imaging. In various embodiments, the fluorescence agent may be injected into a vein, artery, microvasculature (e.g., a capillary bed) or a combination thereof of the subject such that it circulates in the microvasculature. In embodiments in which multiple fluorescence agents are used, such agents may be administered simultaneously, e.g. in a single bolus, or sequentially, e.g. in separate boluses. In some embodiments, the fluorescence agent may be administered by a catheter. In certain embodiments, the fluorescence agent may be administered to the subject less than an hour in advance of performing the measurement according to the various embodiments. For example, the fluorescence agent may be administered to the subject less than 30 minutes in advance of the measurement. In yet other embodiments, the fluorescence agent may be administered at least 30 seconds in advance of performing the measurement. In still other embodiments, the fluorescence agent may be administered contemporaneously with performing the measurement as described in connection with the various embodiments.

In another aspect, the method may exclude any step of administering the fluorescence agent to the subject.

The fluorescence agent may be provided as a lyophilized powder, solid, or liquid. In certain embodiments, the fluorescence agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence agent may be reconstituted with water immediately before administration. In various embodiments, any diluent or carrier which will maintain the fluorescence agent in solution may be used. As an example, in certain embodiments where the fluorescence agent is ICG, it may be reconstituted with water. In some embodiments, once the fluorescence agent is reconstituted, it may be mixed with additional diluents and carriers. In some embodiments, the fluorescence agent may be conjugated to another molecule, e.g., a protein, a peptide, an amino acid, a synthetic polymer, or a sugar e.g., to enhance solubility, stability, imaging properties or a combination thereof. Additional buffering agents may optionally be added including Tris, HCl, NaOH, phosphate buffer, HEPES.

In various embodiments, the fluorescence agent may be administered in various concentrations to achieve a desired circulating concentration in the blood. For example, when the fluorescence agent is ICG, it may be administered at a concentration of about 2.5 mg/mL to achieve a circulating concentration of about 5 $\mu$M to about 10 $\mu$M in blood. In various embodiments, the upper concentration limit for the administration of the fluorescence agent is the concentration at which the fluorescence agent becomes clinically toxic in circulating blood, and the lower concentration limit is the instrumental detection limit for detecting the fluorescence agent in circulating blood. In various other embodiments, the upper concentration limit for the administration of the fluorescence agent is the concentration at which the fluorescence agent becomes self-quenching. In further embodiments, a lower concentration limit for the administration of the fluorescence agent is the concentration at which the fluorescence agent becomes too difficult for conventional imaging technology to detect. For example, when the fluorescence agent is ICG, the circulating concentration of the fluorescence agent may range from 2 $\mu$M to about 10 mM.

The method for measuring the time-varying change in the amount of blood in the tissue volume further comprises acquiring the time-varying light intensity signal during the pulsatile flow of the blood through the tissue volume. In various embodiments, the pulsatile flow arises from a cardiovascular pressure pulse, which may be generated by a heartbeat or simulated heartbeat (e.g., by using a blood pump). The pulsatile flow comprises a diastolic phase and a systolic phase. Furthermore, the diastolic and systolic phases resemble a conventional photoplethysmogram.

The method yet further comprises processing the acquired time-varying light intensity signal (e.g., a time-varying fluorescent light intensity signal) to provide a measurement of the time-varying change in the amount of blood in the tissue volume wherein a modified Beer-Lambert law is applied at the diastolic and systolic phases. The modified Beer-Lambert law for emitted fluorescent light may be written as:

$$\Delta L = \ln[(I_e\Phi - I_m / I_e\Phi - I_p)](\varepsilon C)^{-1}$$

wherein $\Delta L$ is a change in aggregate blood layer thickness within a given tissue volume, $I_e$ is an intensity of an excitation light exciting the fluorescence agent, $\Phi$ is a quantum efficiency of the fluorescence agent, $I_m$ is an intensity of the time-varying light intensity signal during the diastolic phase minimum of the pulsatile flow of the blood through the tissue volume, $I_p$ is an intensity of the time-varying light intensity signal during the systolic phase maximum of the pulsatile flow of the blood through the tissue volume, $\varepsilon$ is a molar absorption coefficient for the fluorescence agent, and C is an instantaneous molar concentration of the fluorescence agent in the blood.

Figure 2:
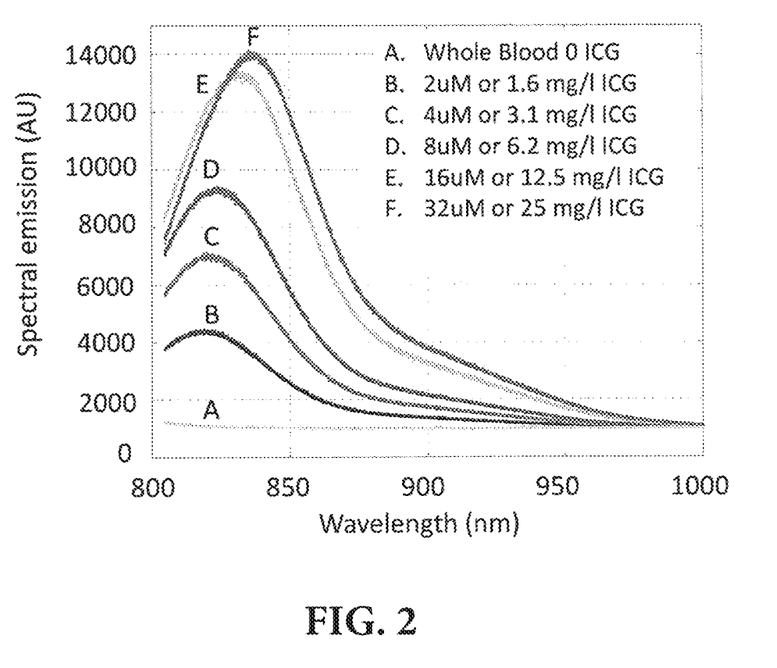
FIG. 2 shows fluorescence emission spectra of indocyanine green (ICG) dye shifting to longer wavelengths with increasing molar concentration of the dye in blood according to an embodiment.

As demonstrated in FIG. 2, the emission spectrum for ICG dye in whole blood is different for each different molar concentration of the dye. In various embodiments, the instantaneous molar concentration of the fluorescence agent is determined by utilizing a concentration-mediated change in a fluorescence emission spectrum of the fluorescence agent. The concentration-mediated change includes a monotonic spectral shift in the fluorescence emission spectrum of the fluorescence agent.

Figure 3:
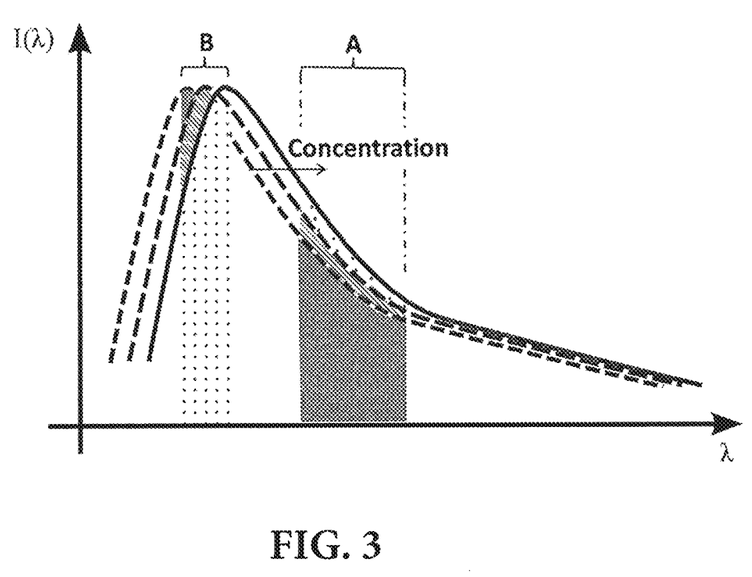
FIG. 3 illustrates an embodiment in which an instantaneous molar concentration of the fluorescence agent in the blood is determined by utilizing a spectral shift in the fluorescence emission spectrum of the fluorescence agent where first and second spectral bands are selected such that one of the first and second intensities varies monotonically with concentration, and one of the first and second intensities is unchanged with concentration.

In various embodiments, utilizing the concentration-mediated change in the fluorescence emission spectrum of the fluorescence agent comprises selecting first and second spectral bands of a fluorescence emission spectrum of the fluorescence agent (e.g., as is shown in FIG. 3), acquiring first and second intensities of fluorescence emission integrated over wavelengths in the first and second spectral bands respectively, calculating a ratio of the first and second intensities, and deriving a value for C in the modified Beer-Lambert law from the calculated ratio.

In various embodiments, the first and second spectral bands may be selected in a number of ways. According to an embodiment, the first and second spectral bands are selected such that one of the first and second intensities varies (increases or decreases) monotonically with C, and one of the first and second intensities is unchanged with C. For example, as is illustrated in FIG. 3, the intensity of fluorescence emission integrated over wavelengths for any bands selected in range B will remain nominally unchanged with increasing concentration of the fluorescence agent. Furthermore, the intensity of fluorescence emission integrated over wavelengths for any bands selected in range A will decrease with C. Consequently, the ratio of intensities of bands from A/B will decrease with C.

Figure 4:
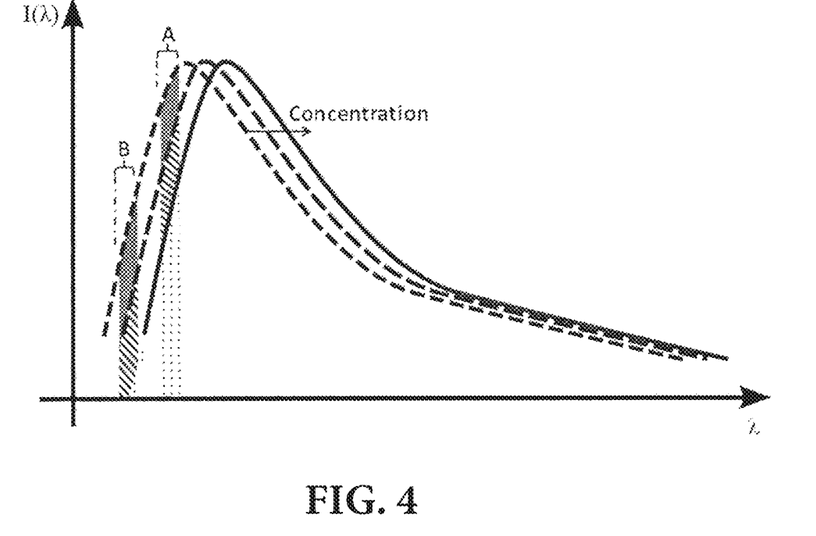
FIG. 4 illustrates an embodiment in which an instantaneous molar concentration of the fluorescence agent in the blood is determined by utilizing a spectral shift in the fluorescence emission spectrum of the fluorescence agent where first and second spectral bands are selected such that the first and second intensities increase monotonically with concentration, but at different rates.

According to another embodiment, the first and second spectral bands are selected such that the first and second intensities decrease monotonically with C, but at different rates. For example, as is illustrated in FIG. 4, the intensity of fluorescence emission integrated over wavelengths for any bands selected in range B will decrease with C, but the intensity of fluorescence emission integrated over wavelengths for any bands selected in range A will decrease more slowly with C. Consequently, the ratio of intensities of bands from A/B will decrease with C.

Figure 5:
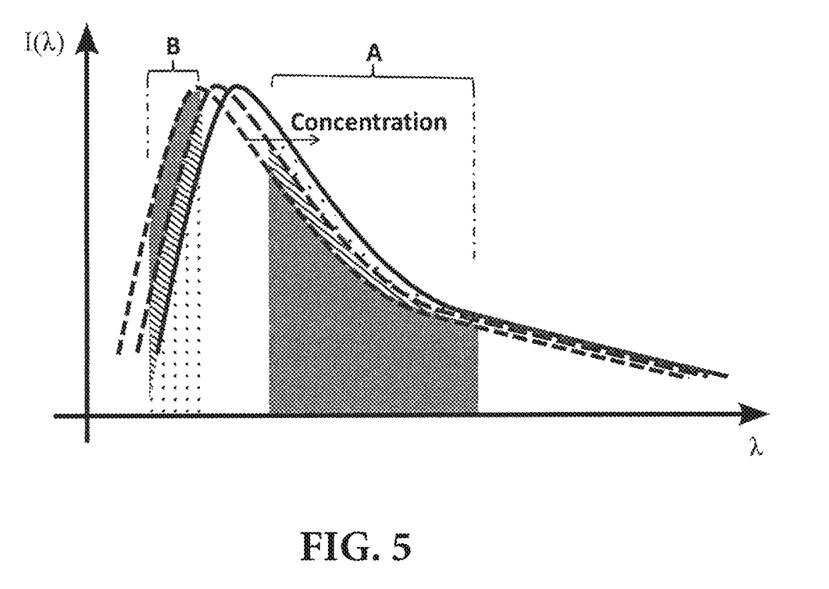
FIG. 5 illustrates an embodiment in which an instantaneous molar concentration of the fluorescence agent in the blood is determined by utilizing a spectral shift in the fluorescence emission spectrum of the fluorescence agent where first and second spectral bands are selected such that the first intensity increases monotonically with concentration, and the second intensity decreases monotonically with concentration.

According to yet another embodiment, the first and second spectral bands are selected such that the first intensity increases monotonically with C, and the second intensity decreases monotonically with C. For example, as is illustrated in FIG. 5, the intensity of fluorescence emission integrated over wavelengths for any bands selected in range B will increase with C, but the intensity of fluorescence emission integrated over wavelengths for any bands selected in range A will decrease with C. Consequently, the ratio of intensities of bands from A/B will decrease with C, but will do so at a greater rate than in the previous embodiments.

In various embodiments, the first spectral band comprises wavelengths ranging from about 780 nm to about 835 nm, or a subset thereof, and the second spectral band comprises wavelengths ranging from about 835 nm to about 1000 nm, or a subset thereof when, for example, the fluorescence agent is ICG.

By selecting the first and second spectral bands as described in connection with the various embodiments, a clinically discernible variation in the ratio is achieved over the range of clinically anticipated concentrations of the fluorescence agent in the circulating blood, and thus the instantaneous molar concentration, C, of the fluorescence agent can be determined.

In various embodiments, the method may further comprise correlating the measurement of the time-varying change in the amount of blood in the tissue volume to a biological parameter, a physiological parameter, a diagnostic parameter, a pathological parameter or a combination thereof. In an alternative embodiment, the method may comprise deriving a measurement of a change in a biological parameter, a physiological parameter, a diagnostic parameter, a pathological parameter or a combination thereof from the measurement of the time-varying change in the amount of blood in the tissue volume. In various embodiments, examples of the biological parameter, the physiological parameter, the diagnostic parameter, the pathological parameter or a combination thereof include those which are indicative or a certain condition of the tissue, a condition of the subject or a combination thereof (e.g., atherosclerosis, oxygenation, cardiac output).

In various other embodiments, the method may exclude correlating the measurement of the time-varying change in the amount of blood in the tissue volume to a physiological parameter, a diagnostic parameter, or a pathological parameter.

In accordance with another aspect of the invention, there is provided an apparatus for measuring the time-varying change in an amount of blood in the tissue volume. The apparatus comprises means for exciting the fluorescence agent in the blood, means for acquiring the time-varying light intensity signal during the pulsatile flow of the blood through the tissue volume (where the pulsatile flow may be caused, for example, by a heartbeat or by means simulating the heartbeat such as, for example, a blood pump), the pulsatile flow having a diastolic and a systolic phase resembling a conventional photoplethysmogram, and means for processing the acquired time-varying light intensity signal to obtain a measurement of the time-varying change in the amount of blood in the tissue volume. A modified Beer-Lambert law is applied at the diastolic and systolic phases to obtain:

$$\Delta L = \ln[(I_e\Phi - I_m / I_e\Phi - I_p)](\varepsilon C)^{-1}$$

as was described in connection with the method embodiments.

In various embodiments of the apparatus, the instantaneous molar concentration of the fluorescence agent, C, is determined by a utilization of a concentration-mediated change, including a monotonic spectral shift, in a fluorescence emission spectrum of the fluorescence agent. In various embodiments, the utilization comprises a selection of first and second spectral bands of fluorescence emission spectrum of the fluorescence agent, an acquisition of first and second intensities of fluorescence emission integrated over wavelengths in the first and second spectral bands respectively, a calculation of a ratio of the first and second intensities, and a derivation of a value for C from the ratio.

According to an embodiment, the selection of the first and second spectral bands is such that one of the first and second intensities varies monotonically with C, and one of the first and second intensities is unchanged with C. According to another embodiment, the first and second intensities increase monotonically at different rates with C. According to yet another embodiment, the first intensity increases monotonically with C, and the second intensity decreases monotonically with C. Examples relating to these embodiments are illustrated in FIGS. 3 to 5. In various embodiments, the first spectral band comprises wavelengths ranging from about 780 nm to about 835 nm, or a subset thereof, and the second spectral band comprises wavelengths ranging from about 835 nm to about 1000 nm, or a subset thereof.

Figure 6:
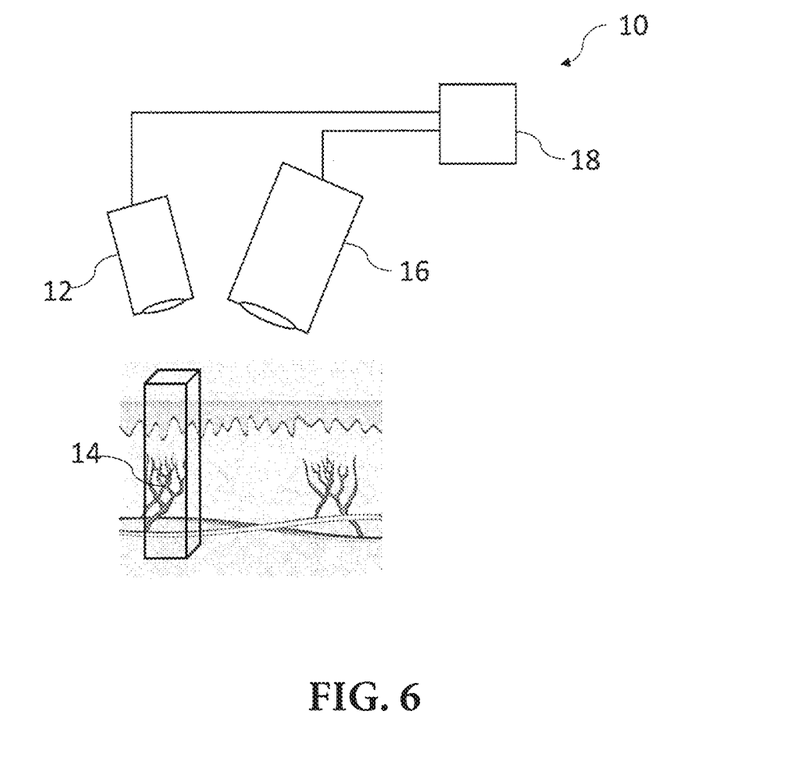
FIG. 6 illustrates an example apparatus for measuring a time-varying change in an amount of blood in a tissue volume according to an embodiment.

Referring to FIG. 6, there is shown schematically an example embodiment of an apparatus 10 for measuring the time-varying change in the amount of blood in the tissue volume. The apparatus 10 comprises means for exciting 12 the fluorescence agent 14 in the blood in the tissue volume, means for acquiring 16 the time-varying light intensity signal during the pulsatile flow of the blood through the tissue volume, and means for processing 18 the acquired time-varying light intensity signal to provide the measurement of the time-varying change in the amount of blood in the tissue volume.

Figure 7:
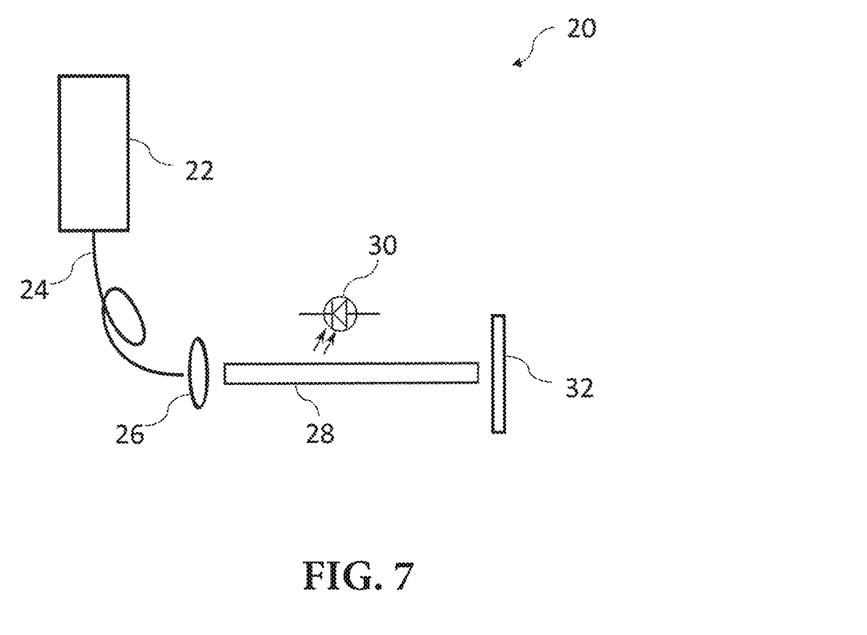
FIG. 7 illustrates an example illumination module according to an embodiment.

In various embodiments, the means for exciting 12 comprises, for example, an illumination module comprising a fluorescence excitation source operatively configured to generate an excitation light having a suitable intensity and a suitable wavelength for exciting the fluorescence agent 14. FIG. 7 shows an example illumination module 20 according to an embodiment. The illumination module 20 comprises a laser diode 22 (e.g., which may comprise, for example, one or more fiber-coupled diode lasers) for providing an excitation light for exciting the fluorescence agent 14 (not shown). Examples of other sources of the excitation light which may be used in various embodiments include one or more LEDs, arc lamps, or other illuminant technologies of sufficient intensity and appropriate wavelength to excite the fluorescence agent 14 in blood. For example, excitation of the fluorescence agent 14 in blood, wherein the fluorescence agent 14 is a fluorescence dye with near infra-red excitation and emission characteristics, may be performed using one or more 793 nm, conduction-cooled, single bar, fiber-coupled laser diode modules from DILAS Diode Laser Co, Germany.

In various embodiments, the light output from the source of the excitation light may be projected through an optical element (i.e., one or more optical elements) to shape and guide the output being used to illuminate the tissue area of interest. The shaping optics may consist of one or more lenses, light guides, and/or diffractive elements so as to ensure a flat field over substantially the entire field of view of the fluorescence emission acquisition module. In particular embodiments, the fluorescence excitation source is selected to emit at a wavelength close to the absorption maximum of the fluorescence agent 14 (e.g., a fluorescence dye such as ICG). For example, referring to the embodiment of the illumination module 20 in FIG. 7, the output 24 from the laser diode 22 is passed through one or more focusing lenses 26, and then through a homogenizing light pipe 28 such as, for example, light pipes commonly available from Newport Corporation, USA. Finally, the light is passed through an optical diffractive element 32 (i.e., one or more optical diffusers) such as, for example, ground glass diffractive elements also available from Newport Corporation, USA. Power to the laser diode 22 itself is provided by, for example, a high-current laser driver such as those available from Lumina Power Inc. USA. The laser may be operated in a pulsed mode during the image acquisition process. In this embodiment, an optical sensor such as a solid state photodiode 30 is incorporated into the illumination module 20 and samples the illumination intensity produced by the illumination module 20 via scattered or diffuse reflections from the various optical elements. In various embodiments, additional illumination sources may be used to provide guidance when aligning and positioning the module over the area of interest.

Figure 8:
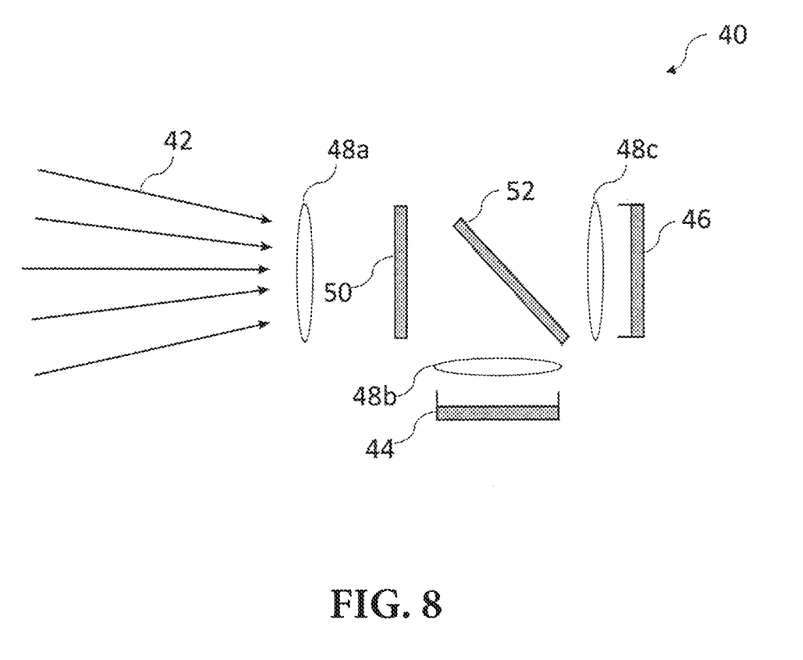
FIG. 8 illustrates an example fluorescence emission acquisition module according to an embodiment.

Referring back to FIG. 6, in various embodiments, the means for acquiring 16 comprises, for example, a fluorescence emission acquisition module for acquiring a fluorescence signal (e.g., the time-varying light intensity signal) from the fluorescence agent 14, the fluorescence emission acquisition module comprising an image sensor. Referring to FIG. 8, there is shown an exemplary embodiment of a fluorescence emission acquisition module 40 for acquiring the fluorescence signal such as the time-varying light intensity signal from the fluorescence agent 14 (not shown). As is shown in FIG. 8, the fluorescence emission 42 from the fluorescence agent 14 in blood (not shown) is collected and focused onto a 2D solid state image sensor (e.g. an image sensor 44 and an image sensor 46) using a system of imaging optics 48a, 48b and 48c. The solid state image sensor may be a charge coupled device (CCD), a CMOS sensor, a CID or similar 2D sensor technology. An optical filter 50 (which may comprise a plurality of optical filters in various arrangements) is used to remove residual and reflected excitation light and to ensure that only the fluorescence emission is recorded at the image sensors 44 and 46. In this embodiment, a dichroic optical filter 52 is used to divide the fluorescence emission spectrum of the fluorescence agent 14 into two spectral channels (e.g., first and second spectral bands). In this embodiment, the dichroic optical filter 52 is designed such that the total fluorescence emission is divided generally equally between the two spectral channels, and such that the shorter wavelength channel collects light of wavelengths equal to or shorter than the fluorescence emission maximum, and the longer wavelength channel collects light equal to or longer than the fluorescence emission maximum. The charge that results from the optical signal transduced by the image sensors 44 and 46 is converted to an electrical video signal, which includes both digital and analog video signals, by the appropriate read-out and amplification electronics in the fluorescence emission acquisition module 40.

Figure 9:
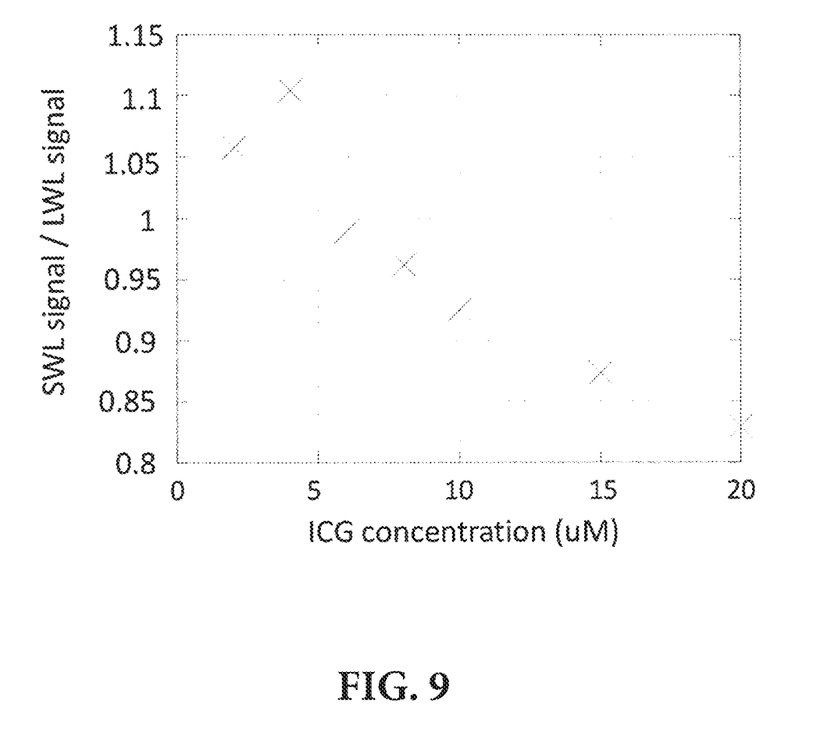
FIG. 9 illustrates an example relationship between a ratio of ICG fluorescence intensities from a first spectral band ranging from about 820 to about 840 nm (where "SWL" denotes a short wavelength) and from the second spectral band ranging from about 840 nm to about 900 nm (where "LWL" denotes a long wavelength) and the instantaneous molar concentration of ICG.

Although only two image sensors 44 and 46 are utilized in the embodiment shown in FIG. 8, the preferred selection of the two spectral bands—where the fluorescence emission over wavelengths in one band monotonically increases with the fluorescence agent concentration and where the fluorescence emission integrated over wavelengths in another band monotonically decreases with the fluorescence agent concentration as shown in FIG. 5—enables the possibility of utilizing the signals transduced by the two sensors in two beneficial ways. Firstly the signal from the two image sensors 44 and 46 may be combined to obtain the total fluorescence image signal intensity. This will enable the highest quality (lowest noise) fluorescent image to be generated. Secondly, the image signal from these two spectral bands can be ratioed on a pixel by pixel basis to determine the instantaneous molar concentration of fluorescence agent 14 in the blood. The molar concentration is an essential parameter in determining the time-varying change in the amount of blood in the tissue volume. The images from the two image sensors 44 and 46 show identical fields of view on a pixel by pixel basis. Furthermore, the range of variation of the ratio as shown in FIG. 9, is increased and the determination of the instantaneous concentration of the fluorescence agent 14 is consequently more accurate by utilizing the selection of the spectral bands as is described in connection with the various embodiments.

Referring back to FIG. 6, in various embodiments, the means for processing 18 comprises, for example, a processor module (not shown) for analyzing time-varying light intensity signals, performing calculations for the plethesmographic computation of the time-varying change in the amount of blood in the tissue volume, outputting the calculated information to an appropriate display and/or recording device, or a combination thereof. In various embodiments, the processor module comprises any computer or computing means such as, for example, a tablet, laptop, desktop, networked computer, or dedicated standalone microprocessor. Inputs are taken, for example, from the image sensors 44, 46 of the emission acquisition module 40 shown in FIG. 8, from the solid state photodiode 30 in the illumination module 20 in FIG. 7, and from any external control hardware such as a footswitch or remote-control. Output is provided to the laser diode driver, and optical alignment aids. In various embodiments, the processor module may have the capability to save image sequences to internal memory, such as a hard disk or flash memory, so as to enable post-processing of acquired data. In various embodiments, the processor module may have an internal clock to enable control of the various elements and ensure correct timing of illumination and sensor shutters. In various other embodiments, the processor module may also provide user input and graphical display of outputs.

Figure 10:
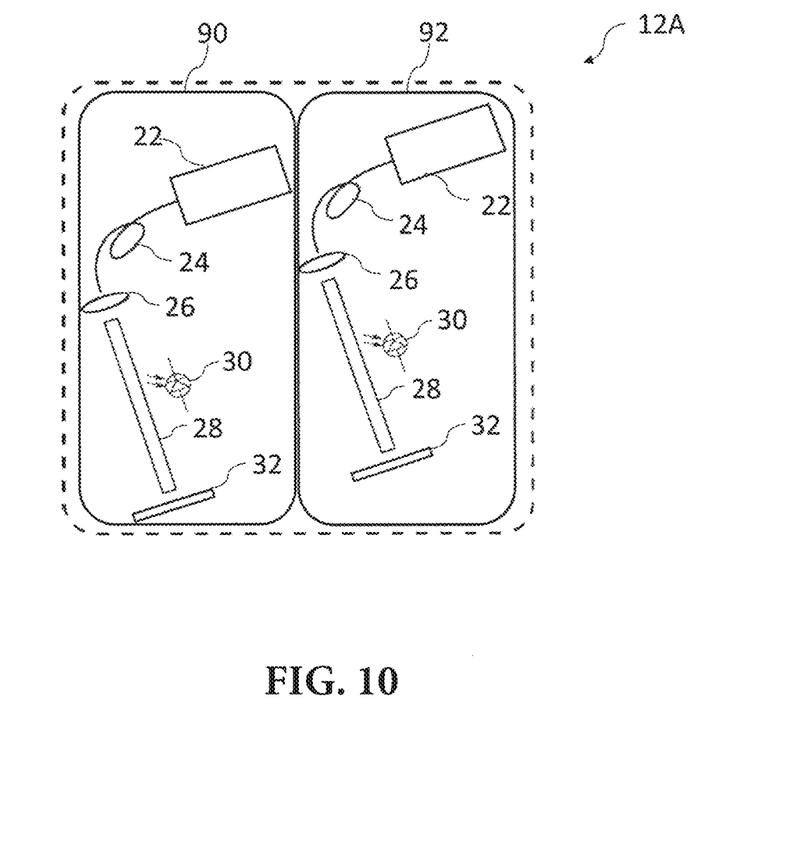
FIG. 10 illustrates an alternative embodiment of the means for exciting for fluorescence excitation of the fluorescence agent of the apparatus in FIG. 6.

In various other embodiments, the apparatus 10 illustrated in FIG. 6, may alternatively comprise the means for exciting 12A for fluorescence excitation of the fluorescence agent 14 (not shown) as illustrated in FIG. 10. The means for exciting 12A comprises an illumination module comprising a first excitation source 90 and a second excitation source 92 for providing an excitation light for exciting the fluorescence agent 14 (not shown). The output from each excitation source is passed through beam shaping and smoothing optics as described in connection with the previous embodiments. In this embodiment, the means for acquiring (not shown) comprises a fluorescence emission acquisition module consisting of fluorescence collecting and imaging optics similar to those described in connection with the previous embodiments, as well as an optical filter for rejection of residual and reflected excitation light (not shown). This system of optics preferably focuses the collected fluorescence onto a single solid-state image sensor, which is read out by the processing module at each frame.

In operation, and with continuing reference to the embodiments in FIGS. 6 to 8, the subject is positioned such that an area of interest is located beneath both the means for exciting 12 comprising the illumination module 20 and the means for acquiring 16 comprising the fluorescence emission acquisition module 40 of the apparatus 10, and such that the illumination module 20 produces a substantially uniform field of illumination across substantially the entire area of interest. In various embodiments, prior to the administration of the fluorescence agent 14 to the subject, an image may be acquired of the area of interest for the purposes of background deduction. For example, in order to do this, the operator may initiate the image acquisition procedure by depressing a remote switch or foot-control, or via a keyboard on the processing module (not shown) of the processing means 18 of the apparatus 10 in FIG. 6. As a result, the excitation source (e.g., the laser diode 22 of the illumination module 20 in FIG. 7) is turned on and begins the shutter sequence for the image sensors (e.g., image sensors 44, 46 of the fluorescence emission acquisition module 40 in FIG. 8). When operating in the pulsed mode of the embodiment, each of the image sensors is read out simultaneously with the laser pulses. In this way, maximum fluorescence emission intensity is recorded, and signal-to-noise ratio is optimized. In this embodiment, the fluorescence agent 14 is administered to the subject and delivered to the area of interest via arterial flow. Image acquisition is initiated, for example, shortly after administration of the fluorescence agent 14, and images of the fluorescence returned from substantially the entire area of interest are acquired throughout the ingress of the fluorescence agent 14. The fluorescence emission from the area of interest is collected by the front imaging optics of the fluorescence emission acquisition module 40. Residual and reflected excitation light is attenuated by the optical filters (e.g., optical filter 50 in FIG. 8).

In the embodiment in FIG. 8, the dichroic optical filter 52 is used to divide the total fluorescence acquired into two selected spectral channels, as is described in connection with the various embodiments. In a single exposure, the images recorded by each sensor 44 and 46 are read out and sent to the processor module (not shown) of the processing means 18 of the apparatus 10 shown in FIG. 6. In various embodiments, the processor module may perform averaging over adjacent pixels in each frame, as well as over multiple successive frames prior to performing any calculations of perfusion. The images recorded in each of the two spectral channels are compared, and the ratio of fluorescence intensity in each channel is calculated over a kernel of the field of view. The kernel may be a single pixel or an array of pixels in the field of view. Based on the calculated ratio, and on a previous calibration of the apparatus, the concentration of ICG within the kernel is calculated. The combined signal from both image sensors 44 and 46 is then used, together with a measurement of the optical illumination intensity as measured by the sampling solid state photodiode 32 within the illumination module 20 in FIG. 7 to calculate the total fluorescence intensity, and determine the volume of blood in the kernel via an application of the modified Beer-Lambert law as is described in connection with the various embodiments. This processing is repeated over substantially the entire field of view, and the resulting measurement of perfusion (blood flow) is displayed to the user on demand as, for example, a grayscale or false color image, or stored for later analysis.

In yet further aspects, there is provided a kit for measuring a time-varying change in an amount of blood in a tissue volume, the kit comprising the apparatus as was described above in connection with the various embodiments, and a fluorescence agent such as, for example, ICG as was described above in connection with the various embodiments.

In yet further aspects, there is provided a fluorescence agent for use in a method for measuring a time-varying change in an amount of blood in a tissue volume of a subject, the various aspects of the method being described above.

While the present invention has been illustrated and described in connection with various embodiments shown and described in detail, it is not intended to be limited to the details shown, since various modifications and structural changes may be made without departing in any way from the scope of the present invention. Various modifications of form, arrangement of components, steps, details and order of operations of the embodiments illustrated, as well as other embodiments of the invention may be made without departing in any way from the scope of the present invention, and will be apparent to a person of skill in the art upon reference to this description. It is therefore contemplated that the appended claims will cover such modifications and embodiments as they fall within the true scope of the invention. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

The invention claimed is:

1. An apparatus for measuring a time-varying change in an amount of blood in a tissue volume, the apparatus comprising:
    an illuminator configured to excite a fluorescence agent in the blood;
    an image sensor configured to acquire a time-varying light intensity signal during a pulsatile flow of the blood through the tissue volume, the pulsatile flow having a diastolic and a systolic phase; and
    one or more processors configured to:
        determine an instantaneous molar concentration of the fluorescence agent in the blood by utilizing a concentration-mediated change in a fluorescence emission spectrum of the fluorescence agent;
        process the acquired time-varying light intensity signal to obtain a measurement of the time-varying change in the amount of blood in the tissue volume, wherein processing the acquired time-varying light intensity signal comprises computing a change in an aggregate blood layer thickness in the tissue volume based on the time-varying light intensity signal and the determined instantaneous molar concentration.

2. The apparatus of claim 1, wherein the concentration-mediated change includes a spectral shift in the fluorescence emission spectrum of the fluorescence agent.

3. The apparatus of claim 1, wherein utilizing the concentration-mediated change comprises:
    selecting first and second spectral bands of fluorescence emission spectrum of the fluorescence agent;
    acquiring first and second intensities of fluorescence emission integrated over wavelengths in the first and second spectral bands respectively;
    calculating a ratio of the first and second intensities; and
    deriving a value for the instantaneous molar concentration of the fluorescence agent in the blood from the ratio.

4. The apparatus of claim 3, wherein the selection of the first and second spectral bands is such that:
    (i) one of the first and second intensities varies monotonically with the instantaneous molar concentration of the fluorescence agent in the blood, and one of the first and second intensities is unchanged with the instantaneous molar concentration of the fluorescence agent in the blood;
    (ii) the first and second intensities increase monotonically with the instantaneous molar concentration of the fluorescence agent in the blood but at different rates; or
    (iii) the first intensity increases monotonically with the instantaneous molar concentration of the fluorescence agent in the blood, and the second intensity decreases monotonically with the instantaneous molar concentration of the fluorescence agent in the blood.

5. The apparatus of claim 3, wherein the first spectral band comprises wavelengths ranging from about 780 nm to about 835 nm, or a subset thereof, and the second spectral band comprises wavelengths ranging from about 835 nm to about 1000 nm, or a subset thereof.

6. The apparatus of claim 1, wherein computing the change in the aggregate blood layer thickness in the tissue volume based on the time-varying light intensity signal and the determined instantaneous molar concentration comprises applying a modified Beer-Lambert law at the diastolic and systolic phases to obtain:

$$\Delta L = \ln[(I_e \Phi - I_m)/(I_e \Phi - I_p)](\varepsilon C)^{-1}$$

where:
$\Delta L$ is a change in aggregate blood layer thickness within a given tissue volume,
$I_e$ is an intensity of an excitation light exciting the fluorescence agent in the blood,
$\Phi$ is a quantum efficiency of the fluorescence agent,
$I_m$ is an intensity of the time-varying light intensity signal during the diastolic phase minimum of the pulsatile flow of the blood through the tissue volume,
$I_p$ is an intensity of the time-varying light intensity signal during the systolic phase maximum of the pulsatile flow of the blood through the tissue volume,
$\varepsilon$ is a molar absorption coefficient for the fluorescence agent,
C is the determined instantaneous molar concentration of the fluorescence agent in the blood.

7. The apparatus of claim 1, wherein the illuminator is operatively configured to generate an excitation light having a suitable intensity and a suitable wavelength for exciting the fluorescence agent.

8. The apparatus of claim 7, wherein the illuminator further comprises an optical element operatively configured to shape and guide the excitation light to provide a uniform field of the excitation light across an area of interest comprising the tissue volume.

9. The apparatus of claim 8, wherein the optical element comprises a lens, a light guide, a diffractive element, or a combination thereof.

10. The apparatus of claim 1, wherein the illuminator comprises a first illuminator and a second illuminator.

11. The apparatus of claim 1, further comprising an optical element disposed in front of the image sensor operatively configured to capture, filter, and direct the time-varying light intensity signal produced by the fluorescence agent to the image sensor.

12. The apparatus of claim 1, wherein the one or more processors are configured to cause the illuminator to excite the fluorescence agent in the blood.

13. The apparatus of claim 1, wherein the one or more processors are configured to cause the image sensor to acquire the time-varying light intensity signal.

14. The apparatus of claim 1, wherein the fluorescence agent is indocyanine green (ICG).

15. The apparatus of claim 1, wherein the instantaneous molar concentration of the fluorescence agent in the blood ranges from about 2 µM to about 10 mM.

16. A kit for measuring a time-varying change in an amount of blood in a tissue volume, the kit comprising the apparatus of claim 1 and a fluorescence agent.

17. A method for measuring a time-varying change in an amount of blood in a tissue volume, the method performed at an apparatus comprising an illuminator, an image sensor, and one or more processors, the method comprising:
- exciting, by the illuminator, a fluorescence agent in the blood;
- acquiring, by the image sensor, a time-varying light intensity signal during a pulsatile flow of the blood through the tissue volume, the pulsatile flow having a diastolic and a systolic phase;
- determining, by the one or more processors, an instantaneous molar concentration of the fluorescence agent in the blood by utilizing a concentration-mediated change in a fluorescence emission spectrum of the fluorescence agent;
- processing, by the one or more processors, the acquired time-varying light intensity signal to obtain a measurement of the time-varying change in the amount of blood in the tissue volume, wherein processing the acquired time-varying light intensity signal comprises computing a change in an aggregate blood layer thickness in the tissue volume based on the time-varying light intensity signal and the determined instantaneous molar concentration.

18. The method of claim 17, wherein the concentration-mediated change includes a spectral shift in the fluorescence emission spectrum of the fluorescence agent.

19. The method of claim 17, wherein utilizing the concentration-mediated change comprises:
- selecting first and second spectral bands of fluorescence emission spectrum of the fluorescence agent;
- acquiring first and second intensities of fluorescence emission integrated over wavelengths in the first and second spectral bands respectively;
- calculating a ratio of the first and second intensities; and
- deriving a value for the instantaneous molar concentration of the fluorescence agent in the blood from the ratio.

20. The method of claim 19, wherein the selection of the first and second spectral bands is such that:
- (i) one of the first and second intensities varies monotonically with the instantaneous molar concentration of the fluorescence agent in the blood, and one of the first and second intensities is unchanged with the instantaneous molar concentration of the fluorescence agent in the blood;
- (ii) the first and second intensities increase monotonically with the instantaneous molar concentration of the fluorescence agent in the blood but at different rates; or
- (iii) the first intensity increases monotonically with the instantaneous molar concentration of the fluorescence agent in the blood, and the second intensity decreases monotonically with the instantaneous molar concentration of the fluorescence agent in the blood.

21. The method of claim 19, wherein the first spectral band comprises wavelengths ranging from about 780 nm to about 835 nm, or a subset thereof, and the second spectral band comprises wavelengths ranging from about 835 nm to about 1000 nm, or a subset thereof.

* * * * *